Figure 1:
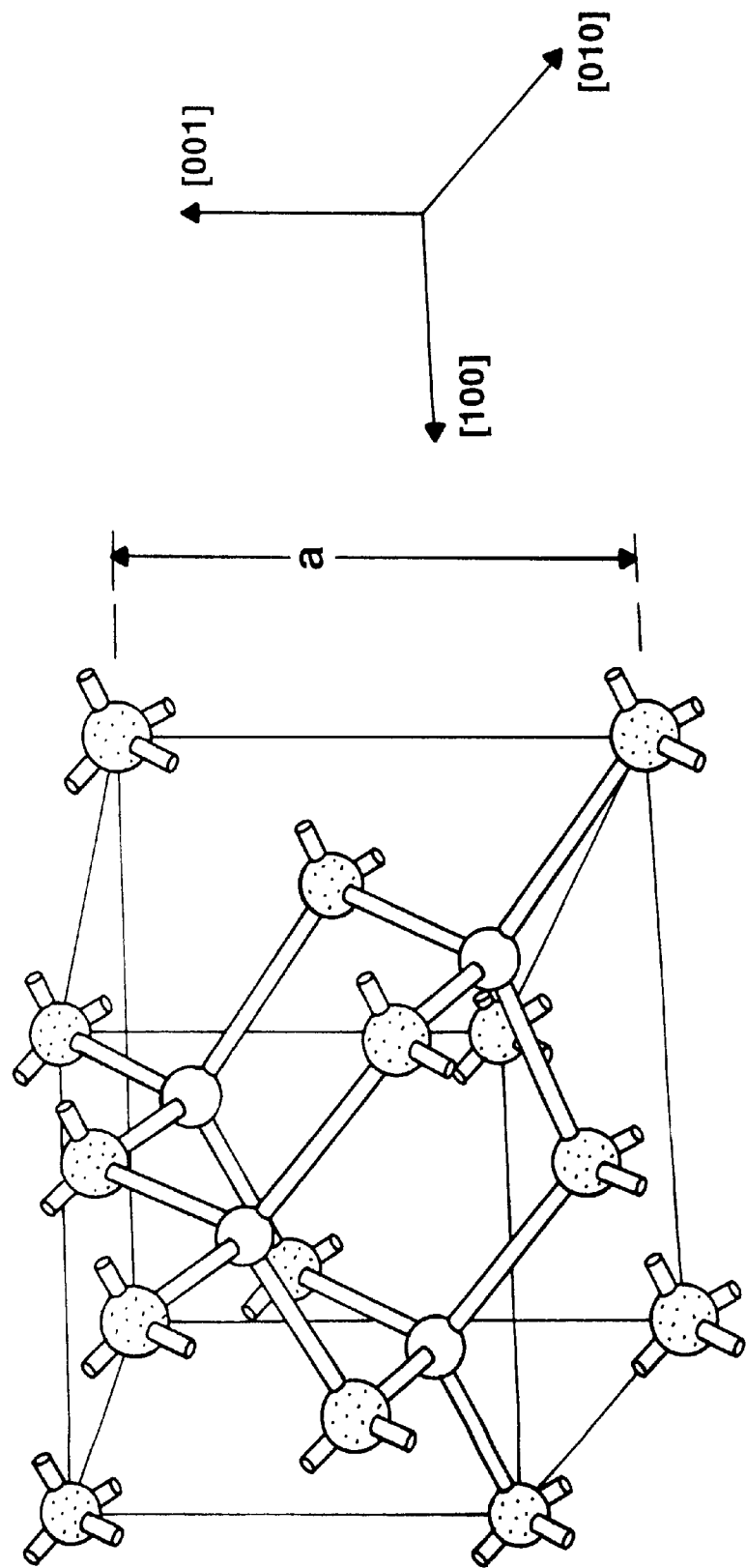

United States Patent [19]
Schnurpfeil et al.

[11] Patent Number: 6,064,070
[45] Date of Patent: May 16, 2000

[54] RADIOACTIVITY ION SOURCES FOR MINIATURIZED ION MOBILITY SPECTROMETERS

[75] Inventors: Roland Schnurpfeil, Bremen; Stefan Klepel, Taucha, both of Germany

[73] Assignee: Bruker-Saxonia Analytik GmbH, Leipzig, Germany

[21] Appl. No.: 09/115,776

[22] Filed: Jul. 14, 1998

[30] Foreign Application Priority Data

Jul. 18, 1997 [DE] Germany .................. 197 30 899

[51] Int. Cl.⁷ .................................................. C23C 8/36
[52] U.S. Cl. ................................. 250/423 R; 258/288
[58] Field of Search ........................ 250/423 R, 288, 250/492.21, 492.1, 492.2, 493.1

[56] References Cited

U.S. PATENT DOCUMENTS

| | | |
|---|---|---|
| 4,024,420 | 5/1977 | Anthony et al. . |
| 4,676,661 | 6/1987 | Keenan et al. . |
| 4,737,234 | 4/1988 | Ruddy ................................. 250/492.1 |
| 5,396,141 | 3/1995 | Jantz et al. . |
| 5,606,213 | 2/1997 | Kherani et al. .................... 310/303 |
| 5,642,014 | 6/1997 | Hillenius . |
| 5,851,315 | 12/1998 | Strathearn et al. ................. 250/303 |

FOREIGN PATENT DOCUMENTS

| | | |
|---|---|---|
| 0476845 A1 | 3/1992 | European Pat. Off. . |
| 0622811 A1 | 11/1994 | European Pat. Off. . |
| 19513459 | 11/1996 | Germany . |
| 53-134199 | 11/1978 | Japan . |
| 2223422 | 4/1990 | United Kingdom . |

OTHER PUBLICATIONS

Amersham Buchler GmbH Product Brochure, Wide Area Reference Sources, *Alpha/Beta Planchet Sources—Type 16/25*, pp. 1–2. No dated.

Francois J. Wuilleumier et al., *Vacuum Ultraviolet Radiation Physics*, Proceedings of the 10$^{th}$ VUV Conference, World Scientific, Paris, Jul. 27–31, 1992, pp. 394–407.

*Industrial Gauging and Analytical Instrumentation Sources,* Amersham, Amersham International plc, Amersham Place, Little Chalfont, Buckinghamshire, England, HP7 9NA, pp. 2 and 29. No dated.

*Primary Examiner*—K. Nguyen

[57] ABSTRACT

The invention relates to a radioactive ion source for generation of low-energy α or β radiation. Both the activity of the source as well as the range of radiation can be adjusted to the respective application. Due to a carrier layer of semiconductive material, release of radioactive substances is prevented.

20 Claims, 3 Drawing Sheets

RADIOACTIVITY ION SOURCES FOR MINIATURIZED ION MOBILITY SPECTROMETERS

FIELD OF INVENTION

Field of invention are miniaturized radioactivity ion sources for the generation of ions by low-energy α or β radiation.

PRIOR ART

Sources for radioactive radiation are decribed, for example, in the brochure "Industrial gauging and analytical instrumentation sources" from Amersham International plc, England (July 1996). On page 29, a tritium source for low-energy β radiation is described. The tritium is absorbed by a thin titanium layer on a stainless steel or copper foil, with an area of 30*10 $mm^2$ and a thickness of 0.25 mm. Maximum activity is stated as being 500 mCi.

The problem of standard commercial tritium sources consists in the fact that the tritium is only physically absorbed by the metal support material (physisorption) and not solidly chemically bonded (chemisorption).

In a further prospectus (4304/990R1.000) from Amersham Buchler, Braunschweig, alpha/beta reference emitters type 16/25 are offered. These comprise, among other emitters, the alpha emitter Am-241 with activities between 184 Bq and 3 kBq. The radioactive material is homogeneously introduced into the surface of anodized aluminum foil with a diameter of 16 mm and a thickness of 0.3 mm. The thickness of the layer activated from the surface is approx. 5 micrometers.

Another popular alternative is that the radioactive material, e.g. americium oxide, is contained in a gold matrix about 2 micrometers thick between a gold layer about 1 micrometer thick and a cover layer of gold palladium alloy about 2 micrometers thick on a silver carrier about 0.2 mm thick.

The generation of ions is, as the name implies, a fundamental prerequisite for ion mobility spectrometry (IMS). Relatively low-energy, radioactive radiation sources for ionization with a radiation penetration range of several millimeters in ambient air have become established for this purpose.

For miniaturization of an IM spectrometer using methods of microfabrication technology, e.g. on a silicon (Si) basis, the hitherto known ion sources have only limited use however, due to their radiation penetration range, shape and size.

Therefore, radioactive sources are needed which conform to the different, generally reduced geometry and design without losing effective activity. Methods should also particularly be sought for designing the ion source in a manner based on microfabrication technology.

SHORT DESCRIPTION OF THE INVENTION

In a first embodiment of the invention, the problem is solved by producing the ion source out of a supporting semiconductor material with tritium ($^3$H) covalently bonded to its surface.

Up to very high temperatures, the covalent bond prevents the tritium from separating from the source again and possibly reaching the environment. Use of a semiconductive support, also for the ion source, makes it possible to adopt the manufacturing techniques known from well-developed semiconductor technology. In particular, the semiconductive support can assume almost any structure and can be supplied with conductive contacts.

It is preferable that the surface is porous, e.g. by using an amorphous semiconductive layer.

This has the advantage of multiplying the effective surface and, in this way, considerably more tritium can be solidly bonded than to a smooth monocrystal surface.

In a favorable embodiment, the semiconductor is silicon. Silicon technology is especially well developed. Silicon is also well suited for surface hydrogenation (passivation), whereby the standard hydrogen must simply be replaced by the radioactive isotope tritium.

Si crystalizes in a diamond structure. This is identical to the zinc-blende-structure, for which the base consists of atoms of the same type (FIG. 1). Two face centered cubic (fcc) grids slid into one another, whose base atoms are at the positions (0,0,0) and (¼, ¼, ¼), respectively. Let us now look at a Si cube with a volume of 1 $cm^3$. At a Si density of ρ=2.33 $g/cm^3$ and a relative atomic mass of m=28 amu, 1 $cm^3$ Si contains a total of $5*10^{22}$ atoms.

Figure 2:
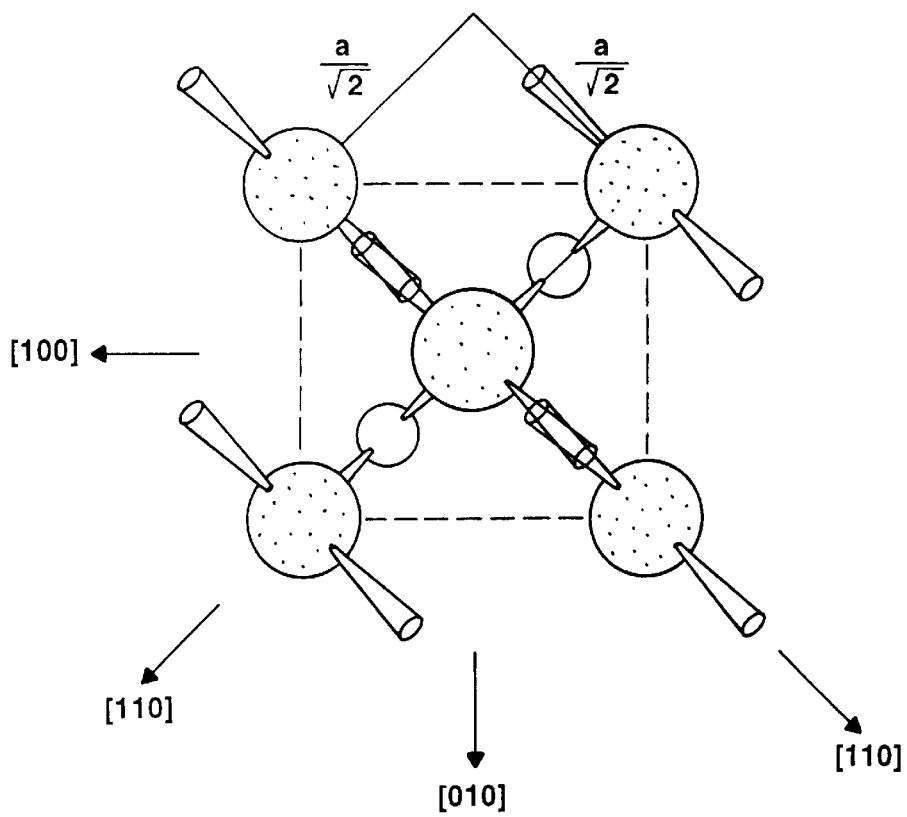
Figure 3:
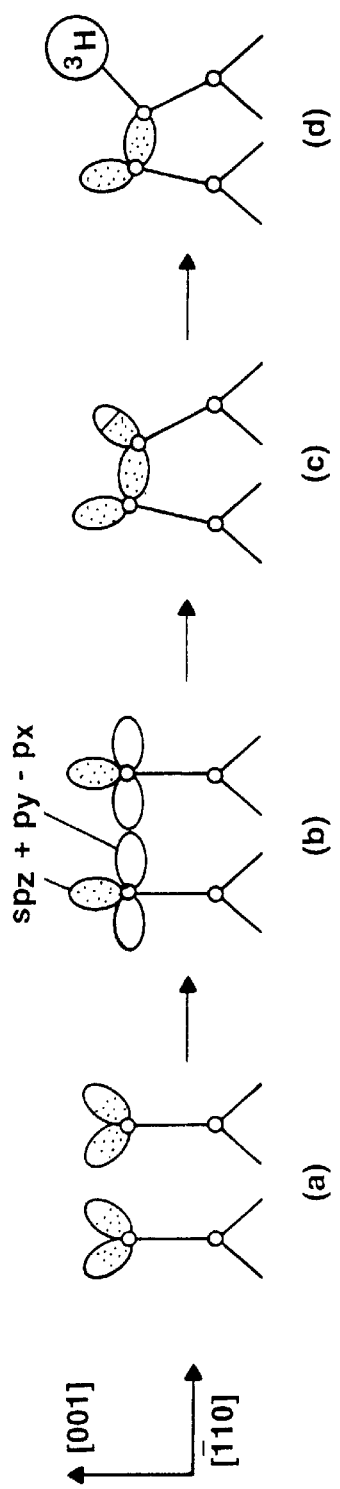

1 $cm^2$ thus contains about $1.4*10^{15}$ Si atoms on the surface. If one now slices through the volume crystal, it becomes apparent that every Si atom found on the surface has two unsaturated bonds, so-called "dangling bonds" (FIG. 2). These are extremely reactive and would, under normal circumstances, bind oxygen. If these surfaces are produced under clean and controlled conditions, such as in a vacuum, the atoms on the surface arrange themselves in such a way as to show as few as possible free unsaturated bonds (FIG. 3).

Taken together, it can be ascertained up to this point that the actual total of possible free bonds for 1 $cm^2$ Si is at an order of magnitude of $10^{15}$. This also takes into consideration that such a surface is not ideally smooth, but also has hills and valleys which further enlarge the actual surface area.

The remaining free bonds still have a reactive potential. A common method to passivate Si surfaces consists of applying hydrogen and allowing it to bond covalently. Depending upon the manufacturing principle, this proceeds in a vacuum simply by gasing with hydrogen or in a wet-chemical process, such as CMOS, by etching (P. Dumas, Vacuum Ultraviolet Radiation Physics, Proceedings of the $10^{th}$ VUV conference, p. 395–407).

Since the chemical behavior of tritium is identical to that of standard hydrogen, it is also possible to apply conventional methods for passivation with hydrogen using tritium instead.

As has been previously determined, 1 $cm^2$ of a Si surface has about $10^{15}$ free bonds which are now saturated by radioactive tritium. Enlargement of the effective surface can be achieved by using porous Si. Factors of 100 are easily achieved here, if necessary even 1,000 or more. We have presumed 100 here, however. In this way, the total of covalently bonded tritium atoms increases to $10^{17}$ $cm^{-2}$. Any absorption of radiation by the porous Si itself is also taken care of in this way.

The radioactive disintegration of tritium must now be examined. Tritium has a half life of $T_{1/2}$=12.3 years or $3.88\times10^8$ seconds. In the first several years, approx. $5\times10^{15}$ nuclei disintegrate each year from the $10^{17}$ tritium atoms bonded to 1 $cm^2$ Si. This corresponds to a specific activity of about 160 $MBq/cm^2$ (4.3 $mCi/cm^2$) on the Si surface. The actual value is probably higher since all previous estimates have allowed a large safety margin on the low side. With an actual surface of 3–4 cm², the performance of a conventional $^{63}$Ni source can be achieved (e.g. 555 Mbq/15 mCi at 4 cm²).

The tritium atoms are so solidly and covalently bonded to the silicon surface that a temperature of about 350–400 degrees Celsius would be necessary to release them again. At this temperature, however, the carrier material would also be destroyed. The same applies to other semiconductors.

In a second embodiment of a radioactive ion source adapted to microfabrication technology, appropriate radioactive materials are implanted in the form of ions into the material of a carrier at a certain distance from the surface. The advantage here is that the penetration range of radioactive radiation in air above the surface can be adjusted via the implant depth and can be adapted to the geometry of the IM spectrometer.

Ion implantation is currently used as a standard method for doping semiconductors or in producing buried layers of metals in silicates. In this invention, the radioactive metal atoms are ionized, then accelerated and shot onto the surface. Depending on the energy of the ions, the metal atoms gather at a specific material depth with Gaussian distribution. A brief intensive tempering step regenerates the crystal, though it can also lead to extremely sharp transitions between pure and doped semiconductor material at appropriate parameters.

For example, $^{241}$Americium is an alpha emitter. With an alpha particle energy of approx. 5.4 MeV, the penetration range of this radiation in air is about 4 cm. For miniaturization of the ion production compartment in the IMS, this penetration range is too high. If the emitter is however buried in some other material than air, the range of this radiation is reduced. According to Bragg and Kleemann's rule, the range of the alpha particles is $R_m = R_{air} \, cm^{1/2}/\rho$.

Here $R_m$ and $R_{air}$ are the ranges in the material or air, m the relative atomic mass of the material, $\rho$ its density and $c=3.2\times10^{-4}$ g cm$^{-3}$ is a constant. With the values for silicon, a total penetration range of 85 $\mu$m in metal thus results. This depth is within the reach for ion implantation. However, the objective is not that no radiation leave the crystal, but rather that its range only is reduced. Implantation at a depth of 60 $\mu$m should thus still allow a medium range of approx. 1 cm. At the same time however, a considerable reduction in radiation intensity must be taken into account.

Relating again to a base area of 1 cm², the thickness of the doped/implanted layer is once again crucial. According to the above considerations, this should be about (10-)20 $\mu$m. The pertinent active volume is thus 0.002 cm³. Depending on the material, ion implantation can dope up to a maximum doping density of $10^{22}$ ions/cm³. A value of $10^{21}$ will be selected here for the prurpose of this consideration.

$^{241}$Americium has a half life of approx. 432.6 years. Thus $1.6\times10^{18}$ nuclei disintegrate each year, which results in a specific activity for our material of $5*10^{10}$ Bq/cm³. Since our layer is only 0.002 cm³, activity is accordingly reduced to $10^8$ Bq/cm² on the active area. If we assume a radiation loss factor of about 100 in the Si, the source is still within the range of 1 Mbq/cm². Indeed, the actual value will be higher, since the assumptions have been safely made on the low side. By increasing the implant rate to a maximum of Am$_2$Si and widening the layer of implanted material, the required activity could be adjusted as necessary within the scope of certain limits.

Preferably, the implanted ions are alpha emitters, particularly $^{241}$Am. The advantage of this is that their range can be adapted well via the implant depth to the dimensions of an ion production compartment in an IMS.

In a favorable further development of this embodiment, the material on the surface is a semiconductor, particularly silicon. In this way, the ion source can be integrated by implantation directly into a component made of conventional semiconductor material. All advantages of this technology are maintained for this component, especially the fact that it can be manufactured, doped, coated and contacted with high degree of precision.

In other embodiments, other carrier materials can also be used, e.g. metals in which radioactive ions are implanted at a distance from the surface.

The invention also relates to an ion mobility spectrometer with a radioactive ion source according to the invention. Naturally, the characteristics described above and introduced further below need not only be used in the respectively named combination but also in any other combination or alone, without leaving the scope of the invention.

SHORT DESCRIPTION OF THE FIGURES

FIG. 1: Unit cell of a crystal in zinc-blende structure.

FIG. 2: Top view of an ideal Si (001) surface.

Figure 4:
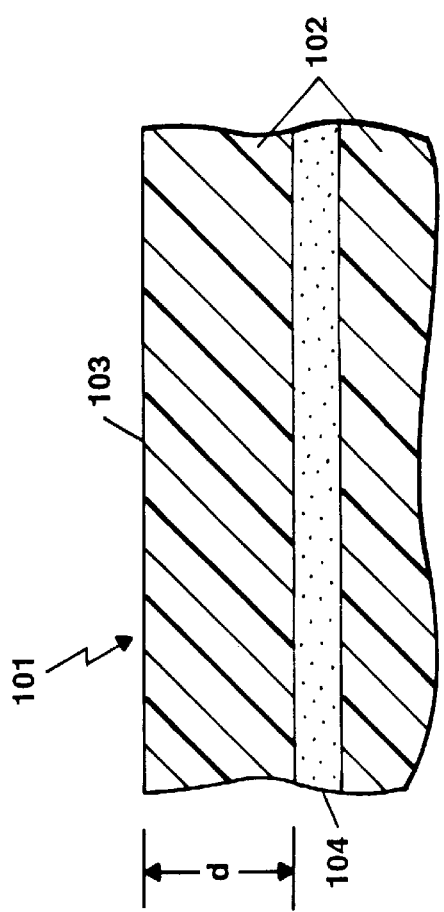

FIG. 3: Change of the bonds at the surface of a Si crystal and covalent tritium bond;

FIG. 4: Implanted doping layer 104 of radioactive ions in the of a carrier layer 102 (with surface 103) of the radiation source 101.

Figure 5:
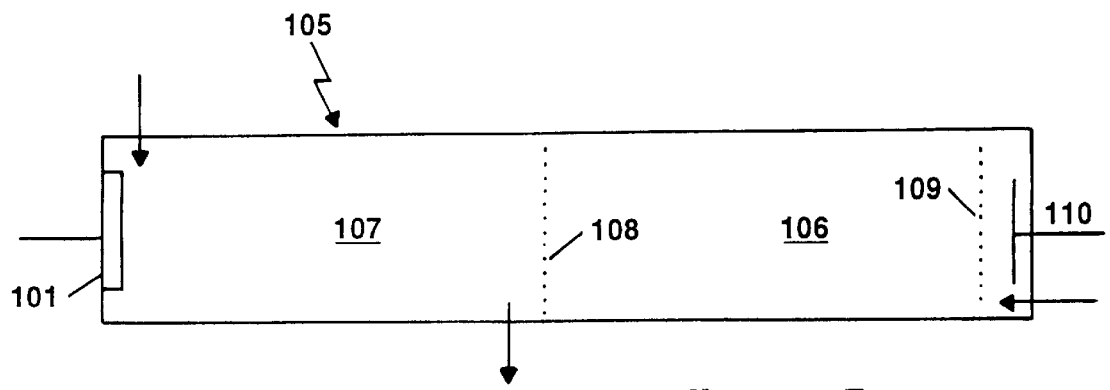

FIG. 5: Ion mobility spectrometer 105, with radiation source 101, ionization and reaction region 107, switchable grid 108, drift region 106, aperture grid 109, and ion collector 110.

MOST FAVORABLE EMBODIMENTS

The invention is explained more closely using examples of embodiments and the drawings. Specifically, FIG. 1 shows the elementary silicon cell that was described above as an example of semiconductive material. For Si, the black and white atoms are equivalent and only look differently here for ease of explanation. a is the grid constant. The cartesian coordinate system indicates the crystalographic directions.

FIG. 2 shows a top view of an ideal Si (001) surface. The surface atoms are black, while those of the first volume layer are white. The "dangling bonds" project out of the drawing plane. The surface of a crystal represents an interference of volume structure. To minimize the number of free bonds, the surface is reconstructed. This is represented in FIG. 3 for a Si (001) surface.

Depending on the situation in the volume (a), the bonding conditions at the surface can be generated by dehybridization which leads to the configuration of an ideal surface depicted in (b) and a dimerization which in the end leads to the final, aplanar reconstructed surface (c); other similar reconstructions are also possible according to preparation conditions. According to the reconstruction shown here (c) only half of a free bond results per surface atom instead of two as before (a).

In silicon technology, or semiconductor technology in general, it is common to passivate the remaining free bonds by the addition of hydrogen, for example, which leads on the one hand to a saturation of the bonds, although on the other hand it also bonds the hydrogen very firmly to the semiconductor. The present invention makes use of this fact. By adding the chemically equivalent tritium ($^3$H) instead of hydrogen ($^1$H) for passivation, the tritium atoms can be reliably bonded in or on a solid (d). The covalent bonds are extremely firm, so that there is much less risk than for pure adsorption or inward diffusion, e.g. in a metal, that tritium atoms are released during an increase in temperature and possibly find their way into the environment.

To increase the effective surface and thus the number of free bonds, it is advantageous to use a rough surface, e.g. using an amorphous semiconductor layer. The surface layer which bonds the tritium can be applied to almost any carrier, e.g. made of ceramic or of any semiconductor material. Here the entire range of known and widely developed manufacturing methods in the semiconductor industry can be used. In particular, with a miniaturized IMS cell, a whole series of funcions can be integrated onto a single textured semiconductor component. For example, one wall can form the ionization chamber, electrical contacts, resistor layers and electrodes can be attached.

In FIG. 4, a further embodiment of the invention is represented, extremely schematically. The radioactive atoms of the radiation source 101 are not bonded covalently to the surface 103 of a carrier layer 102, but instead are discretely shot as ions into the carrier material by means of ion implantation, so that they stop at a finite depth d beneath the surface and form a doping layer 104 there. This layer can be defined once again afterward using a tempering step.

As already discussed above, this type of ion source for a miniaturized IMS is especially appropriate for the alpha emitter $^{241}$Am. By adjusting the acceleration voltage for the implant, the depth d of the doping layer can be defined and adjusted quite well beneath the surface. In this way it is possible to adapt the effective range of the alpha radiation above the surface to a miniaturized ionization chamber of the IMS.

Preferably, the carrier layer again consists of a semiconductive material as in the first embodiment example of the invention, particularly silicon, with the above described advantages. In one embodiment example, the emitter is $^{241}$Am, the carrier is Si and the optimal depth d=60 micrometers. The ionization chamber of the IMS then has a linear dimension of about 1 cm.

Since the radioactive atoms are not fixed via a covalent bond to the semiconductor, but instead by injection far below the surface, the carrier material can also be a metal instead of the preferred semiconductor.

The ion source according to the invention is preferably installed in a miniaturized ion mobility spectrometer, as shown in FIG. 5. The characteristics of the invention make it possible to reduce the size of the ionization chamber and integrate the ion source into the ionization chamber in manufacture.

We claim:

1. A radioactive ion source to generate low-energy β radiation comprising a semiconductor substrate with tritium ($^3$H) being chemically covalently bonded to the surface of the semiconductor substrate.

2. The radioactive ion source of claim 1 wherein the surface is porous.

3. The radioactive ion source of claim 2 wherein the semiconductor substrate is silicon.

4. An ion mobility spectrometer comprising a radioactive ion source according to claim 3.

5. The radioactive ion source of claim 1 wherein the semiconductor substrate is silicon.

6. An ion mobility spectrometer comprising a radioactive ion source according to claim 1.

7. A radioactive ion source to generate low-energy α or β radiation comprising a substrate into which radioactive materials are implanted as ions into a layer inside the substrate, the layer having a predetermined distance d from a surface of the substrate such that a portion of the substrate between the layer and said surface absorbs energy from radiation emitted by the implanted radioactive materials so that the radiation has a predetermined penetration range to the side of the substrate adjacent to said surface.

8. The radioactive ion source of claim 7 wherein the radioactive materials emit α particles.

9. The radioactive ion source of claim 8 wherein the radioactive materials comprise $^{241}$Am.

10. The radioactive ion source of claim 9 wherein the substrate comprises a semiconductor material.

11. The radioactive ion source of claim 10 wherein the semiconductor material comprises silicon.

12. The radioactive ion source of claim 7 wherein the substrate comprises a semiconductor material.

13. The radioactive ion source of claim 12 wherein the semiconductor material comprises silicon.

14. The radioactive ion source of claim 7 wherein the distance d is greater than 20 micrometers.

15. The radioactive ion source of claim 7 wherein the distance d is greater than 50 micrometers.

16. The radioactive source of claim 7 wherein the distance d is about 60 micrometers.

17. The radioactive ion source of claim 7 wherein the substrate comprises silicon and the radioactive materials comprise $^{241}$Am.

18. An ion mobility spectrometer comprising a radioactive ion source according to claim 17.

19. An ion mobility spectrometer comprising a radioactive ion source according to claim 18, further comprising an ionization chamber with a linear extension of less than 2 cm in a direction perpendicular to the surface of the substrate.

20. An ion mobility spectrometer comprising a radioactive ion source according to claim 7.

* * * * *